United States Patent [19]

Smith

[11] Patent Number: 4,944,312
[45] Date of Patent: Jul. 31, 1990

[54] DISPOSABLE FACE SHIELD

[76] Inventor: B. Stewart Smith, 9016½ Pico Blvd., Los Angeles, Calif. 90035

[21] Appl. No.: 405,445

[22] Filed: Sep. 11, 1989

[51] Int. Cl.$^5$ .................... A62B 18/08; A41D 13/00
[52] U.S. Cl. .................................. 128/857; 128/858; 128/207.11; 2/9
[58] Field of Search ............... 128/857, 858, 207.11, 128/206.19, 206.21; 2/9, 10

[56] References Cited

U.S. PATENT DOCUMENTS

| | | | |
|---|---|---|---|
| 3,828,366 | 8/1974 | Conrad et al. | 2/9 |
| 4,825,878 | 5/1989 | Kuntz et al. | 128/857 |
| 4,852,185 | 8/1989 | Olson | 2/9 |

*Primary Examiner*—Mickey Yu
*Assistant Examiner*—Kerry Owens
*Attorney, Agent, or Firm*—Philip D. Junkins

[57] ABSTRACT

A face shield assembly for the protection of the eyes and face of a wearer from infectious, hazardous or undesirable substances. The shield assembly includes a semi-flexible forehead support strip joined at its ends to the ends of a semi-flexible protective face panel support strip. The forehead support strip includes a central strip portion, intermediate strip portions foldable to (and extending outwardly from) the central portion, and end strip portions foldable to (and extending outwardly from) the intermediate strip portions. A semi-flexible, transparent protective face panel is affixed at its upper edge portion to the face panel support strip. An elastic head band is affixed at its ends to an end of the forehead support strip and extends through slip fasteners affixed to the central strip portion of the forehead support strip proximate the fold line between the central portion and the intermediate strip portions. When the elastic head band is pulled through the slip fasteners the intermediate strip portions are folded to the end portions of the forehead support strip and the ends of the face panel support strip are held in abutment to the ends of the central strip portion of the support strip. Thereafter, when the head band is placed about the head of the wearer of the eye/face shield assembly the forehead support strip in its central portion forms into an arcuate shape surrounding the forehead of the wearer and supports the protective face panel support strip, with the face panel, in arcuate spaced face protection orientation on the wearer's head.

14 Claims, 2 Drawing Sheets

DISPOSABLE FACE SHIELD

RELATED APPLICATIONS

This application relates to an invention which comprises a simplification of, and an improvement on, the disposable face shields disclosed and claimed in my applications Ser. Nos.: 07/257,213 filed Oct. 13, 1988;, now U.S. Pat. No. 4,867,178 granted Sept. 19, 1989; 07/325,909 filed Mar. 20, 1989; and 07/350,900 filed May 12, 1989.

FIELD OF THE INVENTION

The present invention relates to face shields for the protection of the eyes and face of wearers from accidental exposure to infectious, hazardous and undesirable substances. More particularly, the invention relates to anti-infection shields for the protection of health care workers and professionals and laboratory personnel from accidental exposure to infectious and/or hazardous particulate materials.

BACKGROUND OF THE INVENTION

Health care workers have long recognized that caring for patients with certain diseases poses risks of contracting such diseases. For example, many oases have been reported of accidental transmission of hepatitis B from patients to persons involved in their care. More recently, the life threatening epidemic of Acquired Immunodeficiency Syndrome (AIDS) caused by the Human Immunodeficiency Virus (HIV) has aroused great concern. Although the bulk of the cases of patient to health care worker cross infection have resulted from accidental needlesticks, medical office, hospital, surgical, dental and laboratory personnel are now required to use extreme care in the handling of all patients and body fluids as potentially infected with HIV and other pathogens. Particular attention has been directed to the risk to surgeons and operating room personnel of infection through splashing or splattering of blood or other body fluids onto open wounds, into mouths or into the eyes of such personnel during the performance of surgical procedures.

Current recommendations of the Centers for Disease Control, public health Service of the U. S. Department of Health and Human Services concerning the prevention of HIV transmission in the health care settings show an increasing concern for protection of the eyes (particularly conjunctiva) if aerosolization or splashing of blood or other fluids is likely to occur. Thus, according to the Centers for Disease Control, eye shields should be worn by medical personnel and laboratory workers to prevent blood and other body fluids from splattering into the eyes. An effective eye shield must protect the eyes no matter which direction the wearer faces. Ordinary eyeglasses are not sufficient protection.

It is an object of the present invention to provide a face shield for the protection of the eyes and face of wearers from accidental exposure to infectious, hazardous and undesirable substances.

It is another object of the invention to provide a face shield for the protection of health care workers and professionals and laboratory personnel from accidental exposure to body fluids from infected patients.

It is a further object of them invention to provide a low cost, disposable face shield for health care workers and professionals and laboratory personnel subject to accidental exposure to infectious fluids.

Another object of the invention is to provide a light-weight, protective face shield for a wide variety of workers who may be exposed to infectious, hazardous and undesirable substances.

Still another object of the invention is to provide a light-weight, disposable protective face shield which is readily formed up from a flat packaged form and may be worn over ordinary eyeglasses.

Other objects and advantages of the invention will become apparent from the following summary and detailed description of a preferred embodiment of the invention taken in conjunction with the accompanying drawing figures.

SUMMARY OF THE INVENTION

The present invention relates to a light-weight, disposable face shield for the protection of the eyes and face of wearers from accidental exposure to infectious, hazardous and undesirable substances. It is of particular interest in the protection of health care workers and professionals and laboratory personnel from accidental exposure to body fluids from infected patients. The shield assembly includes essentially: an elongated, semi-flexible forehead support strip; a semi-flexible face protection support strip; and a generally-rectangular, semi-flexible transparent eye/face protection panel. The transparent eye/face protection panel is affixed, in its upper edge portion, to the protection panel support strip of the shield assembly. The forehead support strip at its first and second ends and the protection panel support strip at its first and second ends are attached to one another and such strips are oriented in parallel overlapping alignment. The forehead support strip of the shield assembly has a central portion that is of shorter length than the attached protection panel support strip and foldable intermediate and end portions extending from the central portion of such strip.

An elastic band is attached at its ends to the forehead support strip proximate the attachment junction between the ends of such strip and the ends of the protection panel support strip. The elastic band from the end attachment junctions of the forehead support strip passes through a slip fastener means at the each end of the central portion of the forehead support strip.

To assemble the disposable face shield of the invention from its pre-use, flat packaged and/or storage form, the elastic band is pulled through the slip fastener means until the ends of the protection panel support strip rest adjacent the ends of the central portion of the forehead support strip. This action causes the longer panel support strip to bow outwardly from the shorter central portion of the forehead support strip. When the face shield assembly is then applied to the wearer's head, with the elastic band surrounding the rear of the wearer's head, the normally flat shorter central portion of the forehead support strip forms into a relatively uniform arcuate portion of the forehead strip surrounding the wearer's forehead in comfortable shield supporting fashion. The semi-flexible transparent protective panel of the shield (outwardly spaced from the forehead support strip) in its arcuate shape is positioned to protect the front and sides of the wearer's face from accidental contact with infectious and/or hazardous and particulate materials.

BRIEF DESCRIPTION OF THE DRAWING FIGURES

DETAILED DESCRIPTION OF THE PREFERRED EMBODIMENT

Figure 1:
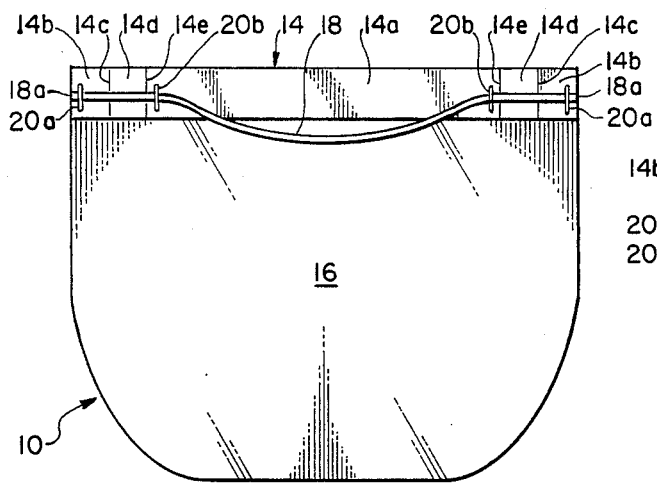
FIG. 1 is a rear view of the eye/face shield of the invention with the forehead support strip, protection panel support strip and transparent eye/face protection panel of the shield in their unformed orientation with the forehead support strip of the shield attached to the protection panel support strip at the ends thereof for flat compact packaging and/or storage.
Figure 2:
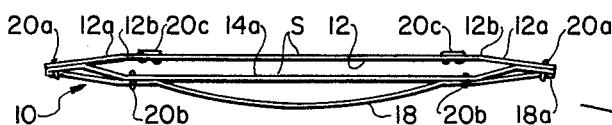
FIG. 2 is a top edge view of the eye/face shield of FIG. 1 showing the protection panel support strip and forehead support strip of the shield in substantially full unfolded position.
Figure 3:
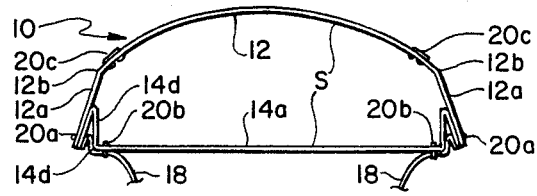
FIG. 3 is a top edge view of the eye/face shield of FIG. 1 showing the protection panel support strip pulled at its ends to the ends of the central portion of the forehead support strip of the shield with the panel support strip thereof bowed outwardly from the central portion of the forehead support strip.

Referring initially to FIG. 1 of the drawing there is illustrated a rear view of the light-weight, disposable face shield 10 of the invention in its unformed or preformed configuration. FIG. 2 of the drawing sheet is a top edge view of the shield 10 in its substantially unformed position and FIG. 3 is a top edge view of the shield in its formed up orientation. In such figures, the shield 10 includes essentially: a head support assembly S comprised of a semi-flexible face protection panel support strip 12 and a semi-flexible forehead support strip 14 joined together at their ends; a generally-rectangular, semi flexible transparent eye/face protection panel 16 affixed at its upper edge portion lo the panel support strip 12; and an elastic head band 18 The semi-flexible support strips 12 and 14 of the head support assembly S may be formed of strips of sheet plastic material or coated paper board. Although the head support assembly S' as shown in the drawing figures, is illustrated as two separate strips joined together at their respective ends and oriented in parallel overlapping alignment. Such assembly may be formed of a single strip of material folded at its mid-point with its ends joined together. The semiflexible, transparent eye/face protection panel 16 is formed of relatively thin optically clear plastic sheet material such as acetate or polyester plastic sheet material.

The transparent eye/face protection panel 16 is affixed at its upper edge portion (by any known means such as by adhesive material, heal sealing, riveting, stapling, etc.) to the panel support strip 12 of the head support assembly S of the shield, joined to the panel support strip 12 at its ends is a forehead support strip 14 of the assembly S. Over the length of the panel support strip 12 of the shield 10 such strip may be comprised of two layers of strip material with the upper edge portion of the protection panel 16 sandwiched therebetween. The central portion 14a of the forehead support strip 14 of the head support assembly S is of shorter length than the protection panel support strip 12 of such assembly. The central portion 14a of the forehead support strip 14 is extended in its length at each end thereof by a relatively short end portion 14b and a relatively short intermediate portion 14d. The strip end portions 14b are each defined by a fold (or score) line 14c and the intermediate strip portions 14d are each defined by a fold line 14c and a fold (or score) line 14e between such intermediate strip portions 14d and the central portion 14a of the forehead support strip 14.

The elastic head band 18 is affixed at each of its ends 18a to respective overlapping ends of the panel support strip 12 and forehead support strip 14 of the head support assembly S as by staple, rivet, eyelet fastener or other means 20a. As shown in FIGS. 1, 2, 3 and 4a a staple 20a maintains the band end 18a attached to the forehead support strip 14 at the terminal end of the end portion 14b and such staple extends through the overlapping ends of both strips 12 and 14 to join such strips. The elastic band 18, as particularly shown in these same figures, extends through slip fastener means 20b at the outer ends of the central portion 14a of forehead support strip 14 proximate the fold (or score) line 14e. The slip fastener means 20b as shown in FIGS. 1–3 and 4b comprises a staple which is applied to the forehead support strip 14 only to the extent that the elastic head band 18 may be pulled therethrough.

Figure 5:
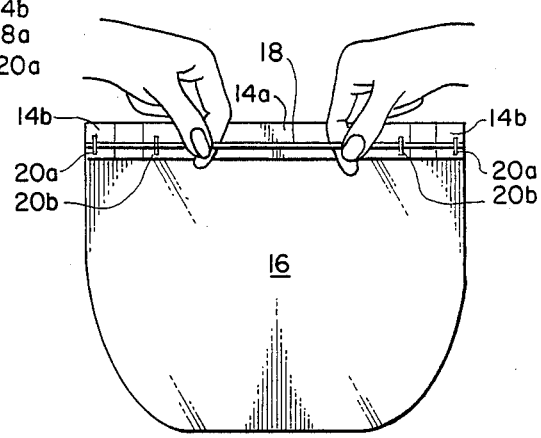
FIG. 5 is a rear view of the eye/face shield of the invention in its unformed orientation with the elastic head support band of the shield held between the thumb and forefinger of each band of the wearer positioned f©r forming up the shield.

In its pre-use flat-packaged and/or shield storage form, the forehead support strip 14 of the head support assembly S of the eye/face shield 10 and the protection panel support strip 12 of the assembly lie adjacent to one-another. In such position, the elastic head band 18 rests freely on the protection panel 16 as shown in FIG. 1. To assemble the disposable face shield 10 of the invention for use by a health care worker, medical professional, laboratory worker or other person having an eye/face protection need the elastic head band 18 is gripped by the thumb and forefinGer of each hand of the wearer as shown in FIG. 5. Thereafter, the band 18 is pulled through the slip fastener means 20b at the ends of the central portion 14a of the forehead support strip 14 (see particularly FIG. 6), thereby moving the end portions 14b and intermediate portions 14d of the strip 14 into collapsed contact with each other (as shown particularly in FIG. 4a) and moving the ends of the central portion 14a of the forehead support strip 14 into near abutment with the ends of the panel support strip 12 with such strip 12 bowing outwardly from strip 14 as shown in FIGS. 3, 4 and 4a.

Figure 6:
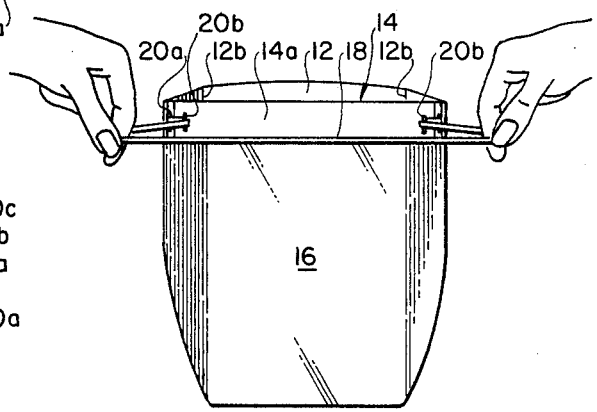
FIG. 6 is a rear perspective view of the eye/face shield of the invention in its formed up orientation prior to application of the shield to the wearer's head.
Figure 4:
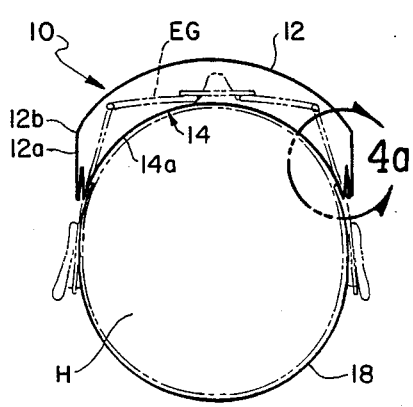
FIG. 4 is a top view of the eye/face shield of the invention in fully assembled (formed up) operative protective position on the wearer's head.
Figure 4A:
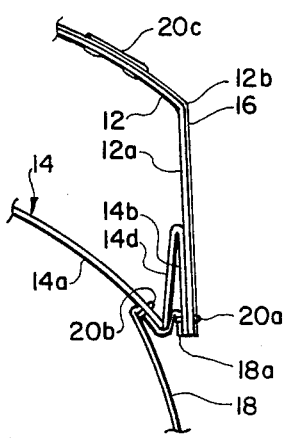
FIG. 4a is an enlarged partial top view of the eye/face shield of FIG. 4 showing in detail) the foregoing and assembled forehead support strip and protection panel support strip of the shield on the right side of the wearer's head at the right edge of the transparent protection panel.

The assembled (formed up) face shield 10 may then be mounted to the wearer's head H, as shown in FIG. 4, with the shorter central portion 14a of forehead support strip 14 of the assembly positioned in arcuate orientation adjacent to the wearer's forehead and the elastic head band 18 positioned about the rear of the wearer's head. When so mounted, the semiflexible, transparent protective panel 16 (and its supporting strip 12) of the shield assembly 10 (outwardly spaced from the forehead support strip 14) forms into full arcuate shape so as to protect the front and sides of the wearer's face (see FIG. 4) from accidental contact with infections and/or hazardous liquids or particulate materials. In FIG. 4 the wearer of the eye/face shield 10 is also shown to be wearing eyeglasses (shown in phantom outline). To assist in the forming up of the eye/face shield of the invention, the protection panel support strip 12 may have relatively short end portions 12a defined by fold (or score) lines 12b so that upon the pulling of the elastic band 18, as shown in FIG. 6, the panel suppOrt strip 12 readily arcs out from the forehead support strip 14.

Figure 7:
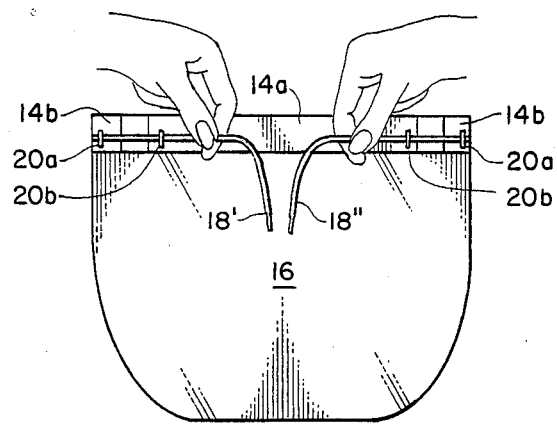
FIG. 7 is a rear view of the eye-face shield of the invention in its unformed orientation with tie strings of the shield held between the thumb and forefinger of each hand of the wearer positioned for forming up the shield.
Figure 8:
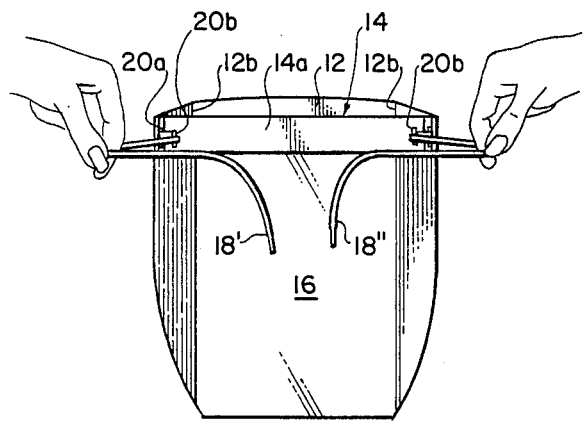
FIG. 8 is a rear perspective view of the eye/face shield of FIG. 7 in its formed up orientation prior to application of the shield to a wearer's head.
Figure 9:
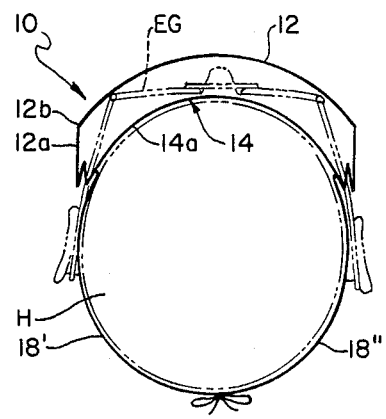
FIG. 9 is a top view of the eye/face shield of FIG. 7 in fully assembled (formed up) operative protective position on the wearer's head with the tie strings tied to one-another at the rear of the wearer's head.

It is to be understood that a number of modifications may be made to the face shield structure of the invention without departing from the spirit thereof. Thus, the slip fastener means proximate the outer ends of the central portion of the forehead support strip may, in addition to staples, comprise pairs of die cut slots or eyelets. Also, the elastic head band of the face shield may be replaced by a pair of tie strings or cords 18'and ~" (as shown in FIGS. 7, 8 and 9) with each string or cord affixed at one of its ends to an end of the head support assembly S as by a staple, rivet, eyelet fastener or like means As with the elastic head band as previously described, the tie strings or cords each pass through slip fastener means proximate the outer ends of the central portion of the forehead support strip. By pulling such cords inwardly through the slip fastener means (see FIG. 8) the end portions and intermediate portions of the forehead support strip are collapsed into contact with one-another and the ends of the central portion of the forehead support strip are moved into near abutment with the ends of the panel support strip with such strip bowing outwardly from the forehead support strip. Thereafter, the face shield may be positioned on the wearer's forehead and the strings or cords 18' and 18" tied together at the rear of the wearer's head (as shown in FIG. 9)

In the specification and drawing figures there has been set forth a preferred embodiment of an improved and simplified light-weight, disposable face shield for the protection of health care workers, medical professionals and laboratory personnel from accidental exposure to body fluids from virus infected individuals and from accidental exposure to other hazardous liquid, and particulate material, in accordance with the invention. Although specific terms have been employed in describing the invention, they are use in a generic and descriptive sense only and not for purposes of limitation, the scope of the invention being defined in the following claims.

What is claimed is:

1. A light-weight, disposable face shield assembly for the protection of the eyes and face of a wearer from accidental exposure to infectious, hazardous and undesirable substances, said face shield assembly comprising:

(a) a semi-flexible forehead support strip and a semi-flexible protective face panel support strip, said forehead support strip being joined at each of its ends to one of the ends of said face panel support strip, said forehead support strip being oriented in parallel relationship to said face panel support strip, and said forehead support strip including a central strip portion, relatively short intermediate strip portions foldable to and extending outwardly from said central portion, and relatively short end strip portions foldable to and extending outwardly from said intermediate strip portions;

(b) a generally rectangular, semi-flexible, transparent protective face panel affixed at its upper edge portion to said face panel support strip and depending downwardly therefrom; and (c) an elastic head band having each of its ends affixed to an end of said forehead support strip proximate the point of joinder of said forehead support strip to said face panel support strip, said head band extending through slip fastener means associated with the central strip portion cf said forehead support strip proximate to fold lines between said central portion and said intermediate portions, the intermediate strip portions of said forehead support strip being foldable to said end portions of said forehead support strip and the ends of said face panel support strip being held in substantial abutment to the ends of the central strip portion of said forehead support strip when said head band is pulled through said slip fastener means and placed in tension about the head of the wearer of said face shield assembly whereby the semi-flexible forehead support strip in its central portion forms into an arcuate shape surrounding the forehead of the wearer and supports the semiflexible protective face panel support strip with said affixed transparent protective face panel in arcuate spaced face protection orientation on the head of the wearer.

2. A light-weight, disposable face shield assembly as claimed in claim 1 wherein the semi-flexible forehead support strip and the semi-flexible protective face panel support strip are formed of sheet plastic material.

3. A light-weight, disposable face shield assembly as claimed in claim 1 wherein the semi-flexible forehead support strip and the semi-flexible protective face panel support strip are formed of coated paper board.

4. A light-weight, disposable face shield assembly as claimed in claim 1 wherein the generally-rectangular, semi-flexible, transparent protective face panel of said face shield assembly is formed of optically clear acetate plastic sheet material.

5. A light-weight, disposable face shield assembly as claimed in claim 1 wherein the generally-rectangular, semi-flexible, transparent protective face panel of said face shield assembly is formed of optically clear polyester plastic sheet material.

6. A light-weight, disposable face shield assembly as claimed in claim 1 wherein the slip fastener means associated with the ends of the central portion of the semi-flexible forehead support strip are staples.

7. A light-weight, disposable face shield assembly for the protection of the eyes and face of a wearer from accidental exposure to infectious, hazardous and undesirable substances, said face shield assembly comprising:

(a) a semi-flexible forehead support strip and a semi-flexible protective face panel support strip, said forehead support strip being joined at each of its ends to one of the ends of said face panel support strip, said forehead support strip being oriented in parallel relationship to said face panel support strip, and said forehead support strip including a central strip portion, relatively short intermediate strip portions foldable to and extending outwardly from said central portion, and relatively short end strip portions foldable to and extending outwardly from said intermediate strip portions;

(b) a generally rectangular, semi-flexible, transparent protective face panel affixed at its upper edge portion to said face panel support strip and depending downwardly therefrom; and (c) a pair of tie strings each having one of its ends affixed to an end of said forehead support strip proximate the point of joinder to said forehead support strip to said face panel support strip, said tie strings extending through slip fastener means associated with the central strip portion of said forehead support strip proximate to fold lines between said central portion and said intermediate portions, the intermediate strip portions of said forehead support strip being foldable to said end portions of said forehead support strip and the ends of said face panel support strip being held in substantial abutment to the ends of the central strip portion of said forehead support strip when said the strings are pulled through said slip fastener means and tie being the head of the wearer of said face shield assembly whereby the semi-flexible forehead support strip in its central portion forms into an arcuate shape surrounding the forehead of the wearer and supports the semiflexible protective face panel support strip with said affixed transparent protective face panel if arcuate spaced face protection orientation on the head cf the wearer.

8. A light-weight, disposable face shield assembly as claimed in claim 5 wherein the semi-flexible forehead support strip and the semi-flexible protective face panel support strip are formed of sheet plastic material.

9. A light-weight, disposable face shield assembly as claimed in claim 5 wherein the semi-flexible forehead support strip and the semi-flexible protective face panel support strip are formed of coated paper board.

10. A light-weight, disposable face shield assembly as claimed in claim 5 wherein the generally-rectangular, semi-flexible, transparent protective face panel of said face shield assembly is formed of optically clear acetate plastic sheet material.

11. A light-weight, disposable face shield assembly as claimed in claim 5 wherein the generally-rectangular, semi-flexible, transparent protective face panel of said face shield assembly is formed of optically clear polyester plastic sheet material.

12. A light-weight, disposable face shield assembly for the protection of the eyes and face of a wearer from accidental exposure to infectious, hazardous and undesirable substances, said face shield assembly comprising:

(a) a semi-flexible forehead support strip and a semi-flexible protective face panel support strip, said forehead support strip being joined at each of its ends to one of the ends of said face panel support strip, said forehead support strip being printed in parallel relationship to said face panel support strip, and said forehead support strip including a central strip portion, relatively short intermediate strip portions foldable to and extending outwardly from said central portion, and relatively short end strip portions foldable to and extending outwardly from said intermediate strip portions;

(b) a generally rectangular, semi-flexible, transparent protective face panel affixed at its upper edge portion to said face panel support strip and depending downwardly therefrom; and (c) flexible head support means for maintaining said face shield assembly on the head of a wearer, said head support means having shield affixation ends each attached to an end of said forehead support strip proximate the point of joinder of said forehead support strip to said face panel support strip, the ends of said head support means extending through slip fastener means associated with the central strip portion of said forehead support strip proximate to fold lines between said central portion and said intermediate portions, the intermediate strip portions of said forehead support strip being foldable to said end portions of said forehead support strip and the ends of said face panel support strip being held in substantial abutment to the ends of the central strip portion of said forehead support strip when said head support means is pulled through said slip fastener means and placed about the head of the wearer of said assembly whereby the semi-flexible forehead support strip in its central portion forms into an arcuate shape surrounding the forehead of the wearer and supports the semi-flexible protective face panel support strip with said affixed transparent protective face panel in arcuate spaced face protection orientation on the head of the wearer.

13. A light-weight, disposable face shield assembly as claimed in claim 12 wherein the flexible head support means comprises an elastic head band having each of its shield affixation ends attached to an end of said forehead support strip proximate the point of joinder of said forehead support strip to said face panel support strip.

14. A light-weight, disposable face shield assembly as claimed in claim 12 wherein the flexible head support means comprises a pair of tie strings each having a shield affixation end attached to an end of said forehead support strip proximate the point of joinder of said forehead support strip to said face panel support strip and a tie end for tie attachment of one string to the other at a point at the rear of the wearer's head.

* * * * *